US011246728B2

(12) United States Patent
Danek (10) Patent No.: US 11,246,728 B2
(45) Date of Patent: Feb. 15, 2022

(54) ANKLE BRACE

(71) Applicant: Mario Danek, Los Angeles, CA (US)

(72) Inventor: Mario Danek, Los Angeles, CA (US)

(73) Assignee: AEGIS BIOMECHANICS, LLC, Beverly Hills, CA (US)

( * ) Notice: Subject to any disclaimer, the term of this patent is extended or adjusted under 35 U.S.C. 154(b) by 966 days.

(21) Appl. No.: 15/357,684

(22) Filed: Nov. 21, 2016

(65) Prior Publication Data

US 2018/0140450 A1    May 24, 2018

(51) Int. Cl.
*A61F 5/01*    (2006.01)
*A61F 5/14*    (2006.01)

(52) U.S. Cl.
CPC .............. *A61F 5/0111* (2013.01); *A61F 5/14* (2013.01)

(58) Field of Classification Search
CPC ........ A61F 5/0111; A61F 5/14; A61F 5/0104; A61F 5/0106; A61F 5/0109; A61F 5/00; A61F 5/0127; A61F 5/0113; A61F 3/08; A61F 5/01–0104; A61F 5/0116; A61F 5/0195; A61F 13/06; A61F 13/064–067; A61F 7/14–1495; A61F 7/18; A61F 7/20; A43B 7/14; A43B 7/1465; A43B 7/1475; A43B 7/1485; A43B 7/1495; A43B 5/00; A43B 5/04; A43B 5/0427–045; A43B 19/00; A43B 23/07
USPC .......................................................... 602/27
See application file for complete search history.

(56) References Cited

U.S. PATENT DOCUMENTS

| 1,318,972 | A |   | 10/1919 | Cook |
| 1,717,432 | A |   | 6/1929  | Botti |
| 2,007,803 | A |   | 7/1935  | Kelly |
| 2,600,957 | A |   | 6/1952  | Bartis |
| 3,073,305 | A | * | 1/1963  | Biggs, Jr. .............. A61F 5/0111 602/65 |
| 3,121,430 | A |   | 2/1964  | O'Reilly |
| 3,298,365 | A |   | 1/1967  | Lewis |
| 3,327,410 | A |   | 6/1967  | Park, Sr. et al. |
| 3,504,668 | A |   | 4/1970  | Boudon |
| 4,495,942 | A |   | 1/1985  | Palumbo |
| 4,628,945 | A |   | 12/1986 | Johnson, Jr. |
| 4,630,600 | A |   | 12/1986 | Spencer et al. |
| 4,753,229 | A |   | 6/1988  | Sutherland |
| 4,825,856 | A |   | 5/1989  | Nelson |
| 4,878,504 | A | * | 11/1989 | Nelson .................. A61F 13/066 602/27 |

(Continued)

FOREIGN PATENT DOCUMENTS

DE    19917822 A1    10/2000
EP    0619102 A1    10/1994

*Primary Examiner* — Michelle J Lee
(74) *Attorney, Agent, or Firm* — K&L Gates LLP (57) ABSTRACT

An exemplary ankle brace includes an inner sleeve, an outer sleeve, a medial guide, a lateral guide, a top guide, and a bottom guide. The brace also includes a medial strap and a lateral strap positioned around the user's ankle between the inner sleeve and the outer sleeve. The medial strap and the lateral strap are configured to tighten the inner sleeve. The brace also includes a collar strap positioned around a tibia and a fibula of the user between the inner sleeve and the outer sleeve. The collar strap is configured to tighten the inner sleeve such that the ankle brace maintains a predetermined height on the user's ankle. The brace also includes a pocket adapted to receive a removable arch support.

14 Claims, 8 Drawing Sheets

(56) References Cited

U.S. PATENT DOCUMENTS

| | | | |
|---|---|---|---|
| 4,982,733 A | | 1/1991 | Broadhurst et al. |
| 5,050,620 A | | 9/1991 | Cooper |
| 5,069,202 A | | 12/1991 | Prock |
| 5,088,478 A | | 2/1992 | Grim |
| 5,430,960 A | | 7/1995 | Richardson |
| 5,445,602 A | | 8/1995 | Grim et al. |
| 5,449,005 A | | 9/1995 | Echols |
| 5,464,384 A | | 11/1995 | Cromartie |
| 5,564,203 A | | 10/1996 | Morris |
| 5,620,413 A | | 4/1997 | Olson |
| 5,657,767 A | | 8/1997 | Nelson et al. |
| 5,678,330 A | | 10/1997 | Van Dyke et al. |
| 5,795,316 A | * | 8/1998 | Gaylord ............... A61F 5/0111 602/27 |
| 6,155,997 A | | 12/2000 | Castro |
| 6,558,339 B1 | | 5/2003 | Graham |
| 6,602,215 B1 | | 8/2003 | Richie, Jr. |
| 6,755,798 B2 | | 6/2004 | McCarthy et al. |
| 6,923,781 B2 | | 8/2005 | Gardner et al. |
| 6,991,613 B2 | | 1/2006 | Sensabaugh |
| 2010/0331750 A1 | * | 12/2010 | Ingimundarson ..... A61F 5/0123 602/26 |
| 2011/0021963 A1 | | 1/2011 | Graddon et al. |
| 2014/0309572 A1 | * | 10/2014 | Heyd ................... A61F 5/0102 602/27 |
| 2015/0290013 A1 | * | 10/2015 | Mueller ............... A61F 5/0123 602/26 |
| 2015/0290017 A1 | * | 10/2015 | Taylor ................. A61F 5/02 602/7 |
| 2015/0351489 A1 | * | 12/2015 | Carandang .......... A43B 3/0031 36/91 |

* cited by examiner

ANKLE BRACE

TECHNICAL FIELD

The present disclosure relates to ankle braces. For example, the present disclosure relates to an ankle brace and ankle brace tightening and anatomically contouring apparatus.

BACKGROUND

There are many parts of the foot and ankle that may need support due to previous injuries or as a precautionary measure during strenuous activities. For example, an individual may use an ankle brace while recovering from or to prevent an injury. Previous techniques to provide foot support included taping the user's foot and/or ankle with medical tape. The medial side of the foot is the inside of the foot. The lateral side of the foot is the outside of the foot. The cuneiforms of the human foot provide the structure of the foot, much like the metacarpals in the human hand. Thus, it follows that the medial cuneiform is the cuneiform on the inside of the foot, and the lateral cuneiform is on the outside of the foot. Within the present disclosure the terms medial and lateral cuneiform do not refer to the bones of the human foot themselves, but rather to the area of the foot where the ankle brace in the present disclosure touches the skin of the foot. Furthermore, the achilles tendon is a tendon located at the back of the foot. For the purposes of the present disclosure, the achilles area refers to the area of the foot where the ankle brace in the present disclosure touches the skin of the foot in the area of the foot where the achilles tendon is located. The current systems employed in the prior art for supporting a users foot and/or ankle with a brace may be improved upon as presently disclosed.

SUMMARY

The present disclosure provides a new and innovative apparatus to be used as an ankle brace. In an exemplary aspect of the present disclosure, ankle brace includes an inner sleeve adapted to fit over a foot, a heel, and an ankle of a user. The ankle brace also includes an outer sleeve adapted to fit over the inner sleeve. The outer sleeve includes a plurality of slots positioned around the outer sleeve. The ankle brace also includes a medial guide, a lateral guide, a top guide, and a bottom guide. The medial guide and the lateral guide are coupled to the inner sleeve. Additionally, the top guide and the bottom guide are coupled to the inner sleeve. The bottom guide is coupled to the inner. The ankle brace also includes a medial strap of a first material and a lateral strap of a second material. The medial strap has a first end and a second end positioned around the user's ankle between the inner sleeve and the outer sleeve. The medial strap is configured to tighten the inner sleeve. The first end of the medial strap begins at an achilles area, and the second end of the medial strap protrudes from a first slot of the plurality of slots in the outer sleeve. The lateral strap of a second material having a first end and a second end positioned around the user's ankle between the inner sleeve and the outer sleeve. The lateral strap is configured to tighten the inner sleeve. The first end of the lateral strap begins at the achilles area, and the second end of the lateral strap protrudes from a second slot of the plurality of slots in the outer sleeve. The ankle brace also includes a collar strap of a third material. The collar strap has a first end and a second end positioned around a tibia and a fibula of the user between the inner sleeve and the outer sleeve. The first end of the collar strap protrudes from a third slot of the plurality of slots in the outer sleeve. The collar strap is configured to tighten the inner sleeve such that the ankle brace maintains a predetermined height on the user's ankle. The medial strap extends from the first end positioned at the achilles area, through the medial guide, through the top guide, over a lateral cuneiform, through the bottom guide, and out from the first slot to the second end of the medial strap. The lateral strap extends from the first end positioned at the achilles area, through the lateral guide, through the top guide, over a medial cuneiform, through the bottom guide, and out from the second slot. The collar strap is configured to move freely between the third slot and a fourth slot of the plurality of slots.

In accordance with another exemplary aspect of the present disclosure, which may be used in combination with the preceding aspect, an ankle brace tightening apparatus includes a first channel, a second channel, and a third channel. The first channel is adapted to receive a medial strap. The first channel includes a first end, a medial guide, a top guide, a bottom guide, and a second end. The first end of the first channel is positioned at an achilles area. The first channel extends from the achilles area, to the medial guide, to the top guide, over a lateral cuneiform area, to the bottom guide, and out from the first slot to the second end of the first channel. The second channel is adapted to receive a lateral strap. The second channel includes a first end, a lateral guide, the top guide, the bottom guide, and a second end. The first end of the second channel is positioned at the achilles area. The second channel extends from the achilles area, to the lateral guide, to the top guide, over a medial cuneiform area, to the bottom guide, and out from the second slot to the second end of the second channel. The third channel adapted to receive a collar strap.

In accordance with another exemplary embodiment of the present disclosure, which may be used in combination with one or more of the preceding aspects, an ankle brace includes an inner sleeve and an outer sleeve. The inner sleeve is adapted to fit over a foot a heel, and an ankle of a user. The outer sleeve is adapted to fit over the inner sleeve. The outer sleeve includes a plurality of slots positioned around the outer sleeve. The ankle brace also includes a first channel, a second channel, and a third channel. The first channel is adapted to receive a medial strap. The first channel includes a first end, a medial guide, a top guide, a bottom guide, and a second end. The first end of the first channel is positioned at an achilles area. The first channel extends from the achilles area, to the medial guide, to the top guide, over a lateral cuneiform area, to the bottom guide, and out from the first slot to the second end of the first channel. The second channel adapted to receive a lateral strap. The second channel includes a first end, a lateral guide, the top guide, the bottom guide, and a second end. The first end of the second channel is positioned at the achilles area. The second channel extends from the achilles area, to the lateral guide, to the top guide, over a medial cuneiform area, to the bottom guide, and out from the second slot to the second end of the second channel. The third channel is adapted to receive a collar strap. The inner sleeve and outer sleeve are coupled together to form an attached area and channel area. The channel area includes the first channel, the second channel, and the third channel. The medial strap is configured to move freely within the first channel, the lateral strap is configured to move freely within the second channel, and the collar strap is configured to move freely within the third channel.

Additional features and advantages of the disclosed apparatus are described in, and may be apparent from, the following Detailed Description and Figures.

DETAILED DESCRIPTION

In general, the ankle brace disclosed herein is designed to wrap around a user's ankle to provide firm yet comfortable ankle support. An example ankle brace includes an inner lining or sleeve and an outer lining or sleeve. The space between the inner and outer lining may include straps configured to securely fasten the brace around the user's foot and/or ankle. The straps are adapted to extend from the outer sleeve of the ankle brace such that the brace may be tightened by pulling the extended ends or tabs and fastening the ends or tabs to the outer sleeve of the ankle brace. Furthermore, the straps may be held in place by guides that are positioned such that the guides allow the user to easily and effectively tighten the ankle brace by pulling on the tabs.

Referring to the Figures, embodiments of an ankle brace are disclosed. As seen in an exemplary ankle brace 100 illustrated in FIG. 1A and FIG. 1B, an outer sleeve 120 is used in conjunction with an inner sleeve 110. The outer sleeve 120 is adapted to fit over the inner sleeve 110. In an example embodiment, the primary aesthetic appearance of the ankle brace 100 may be dominated by the appearance of the outer sleeve 120 because the outer sleeve 120 may cover the entirety of the exterior of the ankle brace 100. In another example embodiment, the outer sleeve 120 may be translucent, giving an entirely different overall appearance to the ankle brace 100. In other embodiments, the outer sleeve 120 may partially cover the inner sleeve 110 thereby increasing breathability of the ankle brace 100. For example, only the inner sleeve 110 may cover the user's foot in locations where the outer sleeve 120 does not extend. Similarly, the inner sleeve 110 may be smaller than the outer sleeve 120, thus leaving some of the user's foot covered by the outer sleeve 120, which may be similarly advantageous for the breathability of the ankle brace 100.

The ankle brace 100 may have various thicknesses. For example, the ankle brace 100 may be thin, similar to Spandex® or a sleeve, which advantageously allows the user to comfortably wear the ankle brace 100 underneath a shoe or boot. In another example embodiment, the ankle brace 100 may be thick, similar to a shin guard or athletic shoe, which advantageously provides more protection to the user and increases durability of the ankle brace 100.

The ankle brace 100 may be made of a single material or a combination of materials. For example, the inner sleeve 110 and outer sleeve 120 may be made from the same material. Conversely, the inner sleeve 110 and the outer sleeve 120 may be made from different materials. In an example embodiment, the ankle brace 100 may include an insulating outer sleeve 120 to protect the user from the cold. In another example embodiment, the ankle brace 100 may include a breathable mesh like outer sleeve 120. For example, the ankle brace 100 may be worn in hot weather, and a thinner and more breathable inner sleeve 110 and/or outer sleeve 120 may be desired. The ankle brace 100 may also include a moisture wicking inner sleeve 110 to keep the user's foot dry when the user's foot perspires. In an example embodiment, the inner sleeve 110 and/or the outer sleeve 120 may be made from materials such as but not limited to mcdavid, polyester (e.g., 2-way or 4-way stretch polyester), cotton blends, nylon. Spandex®, and any combination thereof.

The ankle brace 100 may be made from different materials based on material properties and functionality. In an example embodiment, the inner sleeve 110 may be made from a plurality of materials. For example, the inner sleeve 110 may have a breathable mesh material on the upper portion of the foot, a non-skid material such as dycem on the lower portion of the foot to prevent slipping, and a more rigid material such as rubber or the like on the sides or cuneiform areas of the foot to provide support to the foot. In another example embodiment, the ankle brace 100 may worn beneath a shoe or boot. For example, the user may not want the ankle brace to slip up or down on the user's foot. In such an example embodiment, a non-slip material may be user for the inner sleeve 110 such as but not limited to dycem. In another example embodiment, the outer sleeve 120 may be manufactured from more than one material. For example, the outer sleeve 120 may be made from a breathable mesh material on the upper portion of the foot, a non stick material such as dycem on the lower portion on the foot to prevent slipping, and a more rigid material such as rubber or the like on the sides or cuneiform areas of the foot to provide support to the foot.

In example embodiments, the ankle brace 100 may be adapted to cover various portions of the user's foot and/or ankle. For example, the ankle brace 100 may be adapted to cover a medial side of a user's foot and a lateral side of a user's foot. Placement of openings in the ankle brace 100 may be configured to facilitate putting on and removing the ankle brace 100. In an example embodiment, the ankle brace 100 may include a heel opening 102. The heel opening 102 may facilitate putting on and removing the ankle brace 100. For example, the heel opening 102 may make it easier for the user to put on the ankle brace 100 since the heel sticks out relative to the rest of the foot, especially if the ankle brace 100 is made from a non-elastic material. An inelastic ankle brace may become obstructed by the user's heel when the user attempts to put the ankle brace on and a heel opening 102 mitigates this issue. The heel opening 102 may also advantageously improve breathability of the ankle brace 100. In another example embodiment, the ankle brace 100 may cover a heel of the user's foot.

In another example embodiment, the ankle brace 100 may include a toe opening 104. The toe opening 104 may facilitate putting on and removing the ankle brace 100. For example, the toe opening 104 may make it easier for the user to put on the ankle brace 100 since the toes may travel through most of the ankle brace 100. A user's toes may snag the ankle brace 100 and may obstruct the user from inserting their foot when the user attempts to put the ankle brace 100 on, but the toe opening 104 may mitigate this issue. The toe opening 104 may also advantageously improve breathability of the ankle brace 100. In another example embodiment, the ankle brace 100 may cover the toes of the user's foot. Additionally, the ankle brace 100 may extend up a user's leg just above the ankle. The ankle brace 100 may also extend up to or over the knee of the user. In still other embodiments, the ankle brace 100 may also include various holes or openings in the inner sleeve 110 and/or outer sleeve 120 to improve breathability, comfort, and/or fit of the ankle brace 100. For example, the holes or openings may be configured to improve airflow around the foot when the ankle brace 100 is worn during strenuous activity, such as an athletic event.

In another example embodiment, the inner sleeve 110 and outer sleeve 120 may be manufacturer from an elastic material to facilitate putting on and removing the ankle brace 100. For example, an elastic material such as Neoprene, a polyamide and Spandex® blend (e.g., 66% polyamide and 33% Spandex®), seamless 2-way stretch fabric, 4-way stretch fabric, cotton and polyester blends, and the like would be able to comfortably stretch over the user's ankle, heel, and ore toes. Additionally, the ankle brace 100 may also include tabs or straps to assist the user in pulling the brace onto the user's foot and into proper position. In an example embodiment, straps may be placed at the collar of the ankle brace on the medial and lateral side of the brace. For example, the straps may be used to pull the brace onto the user's foot. In an example embodiment, the straps may be made from nylon (e.g., woven nylon), polyesters, and the like such that the straps have sufficient strength so that they do not rip and lightweight so that the functionality of the ankle brace 100 is not affected.

In an example embodiment, the ankle brace 100 may provide support to the arch, heel, achilles, lateral side, and/or medial side of the user's foot. Support for the foot may be provided in several different ways. For example, support may be provided by rigid inserts made of metal, plastic, polymers, resins, or a similar rigid material. In other embodiments, additional support for various parts of the ankle may be provided in the form of semi-rigid, elastic, gel filled, or compression supports, which may provide pressure to various parts of the foot. For example, a compression style support member may be configured to provide pressure around the ankle of the user. In other embodiments, a compression style support member may wrap around the foot to provide pressure on the lateral cuneiform, medial cuneiform, and arch of the user's foot. Additionally, non-rigid and rigid support members may be used in the ankle brace 100. For example, rigid lateral supports may be positioned on or near the side of the ankle to prevent rolling the ankle and compression style support may be positioned on or near the arch of the foot to provide protection to the area around the arch of the foot.

In another example embodiment, the ankle brace 100 may include inflatable support member. The inflatable support members may be inflated or deflated to vary the amount of pressure or rigidity the user desires. In one embodiment, an arch support member may be inflated or deflated according to a user's needs based on the individual geometry of the user's foot. In another example embodiment, the entire bottom of the ankle brace may include an inflatable, gel-filled, or liquid filled member, which may perform the function of an insole. Such an embodiment may have distinct advantages over a traditional ankle brace because the ankle brace may be adjusted or formed by the user to be more comfortable or to fit the specifics of the user's foot. The ankle brace 100 may also include inflatable supports on the medial and/or lateral sides of the ankle. For example, the medial and/or lateral inflatable supports may be inflated or deflated depending on the amount of support and/or rigidity the user desires or to accommodate another article being worn under the ankle brace 100.

In an example embodiment, the ankle brace 100 may provide protection of the user's foot along with support. For example, the ankle brace 100 may include rigid protection positioned between the inner sleeve 110 and the outer sleeve 120 of the ankle brace 100. The rigid protection may provide protection from strikes of other athlete's feet during activities, such as athletic events. For example, shielding may be placed around the user's ankle to prevent other players from hurting the user's ankle when kicked in a game of soccer. Additionally, protective shielding may be placed over the top of the user's foot to protect the user's foot from heavy items dropped on the user's foot. In an example embodiment, the rigid protection may be in the form of a plate, insert, or shield, which can be fabricated from a wide array of materials, including but not limited to plastics, metals, and/or fabrics. The rigid protection may be removable or replaceable by the user, which may allow the user to insert different types of protection according to the specific use of the ankle brace 100.

Figure 1A:
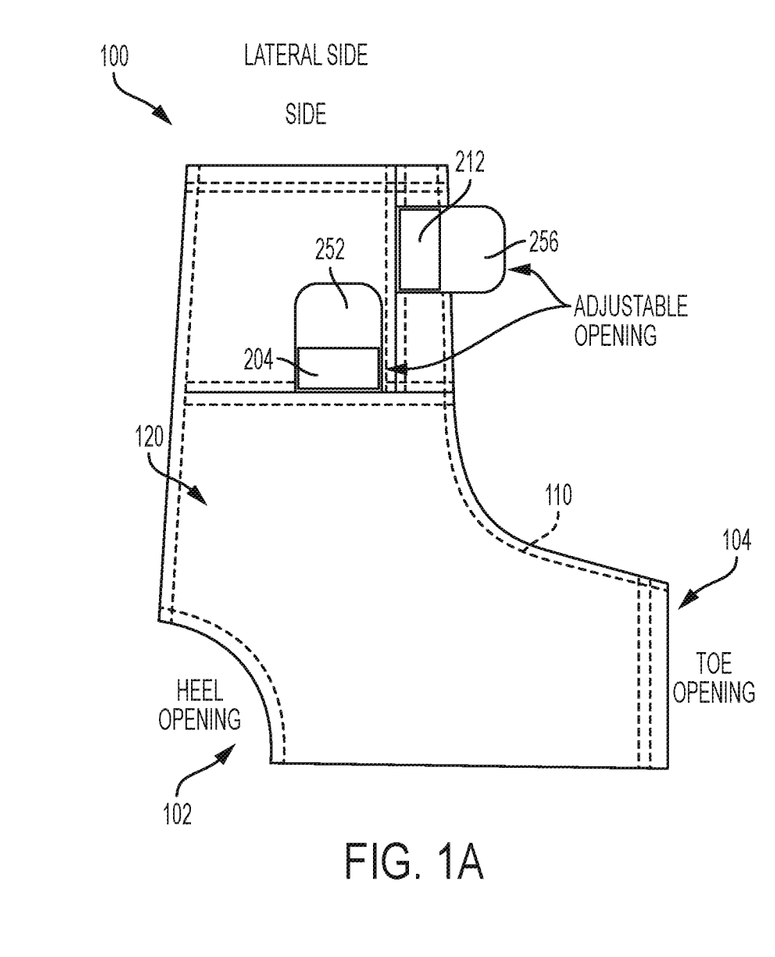
FIG. 1A is a lateral side view of an ankle brace, according to an example embodiment of the present disclosure.
Figure 1B:
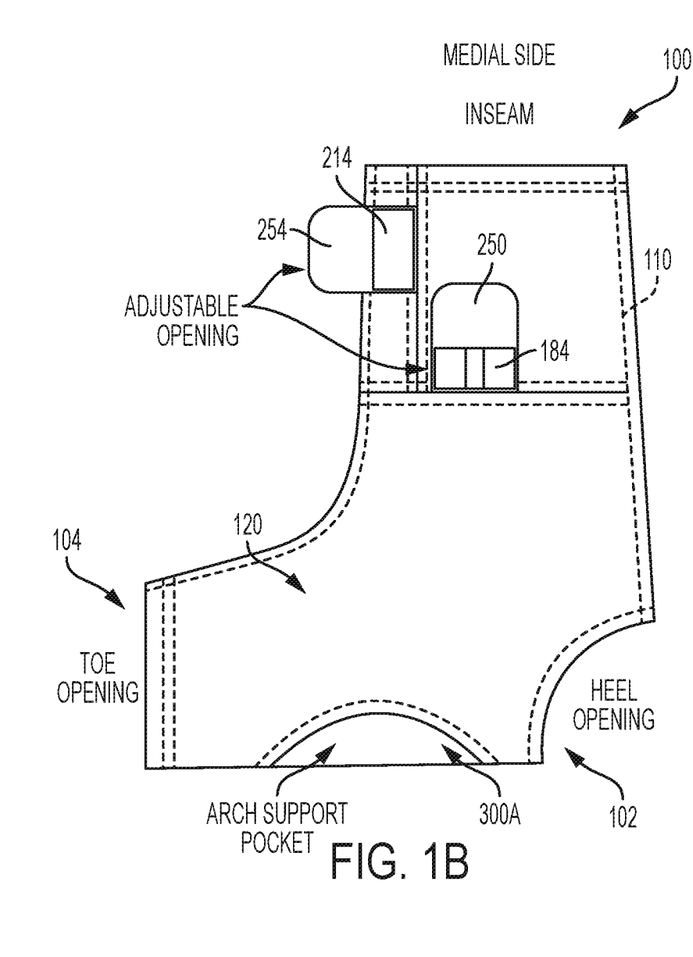
FIG. 1B is a medial side view of an ankle brace, according to an example embodiment of the present disclosure.
Figure 1C:
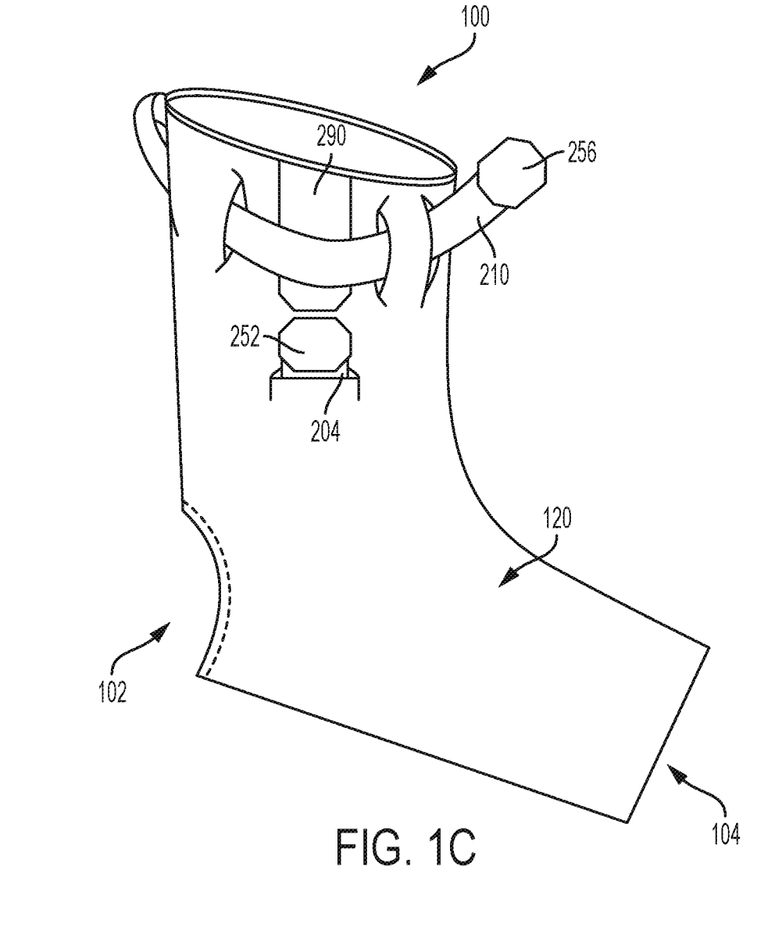
FIG. 1C is a lateral side view of an ankle brace, according to an example embodiment of the present disclosure.
Figure 1D:
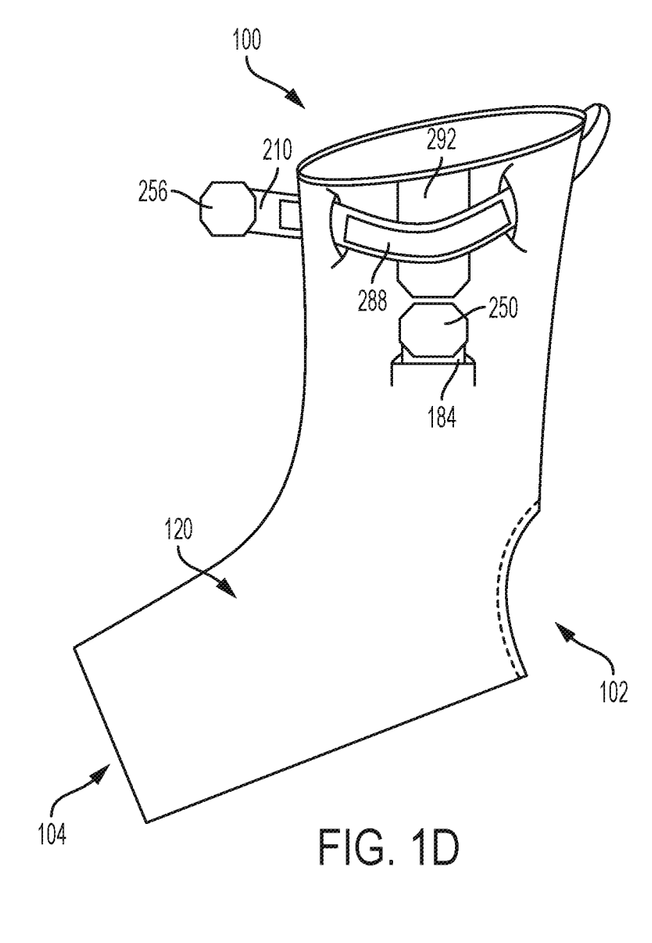
FIG. 1D is a medial side view of an ankle brace, according to an example embodiment of the present disclosure.
Figure 1E:
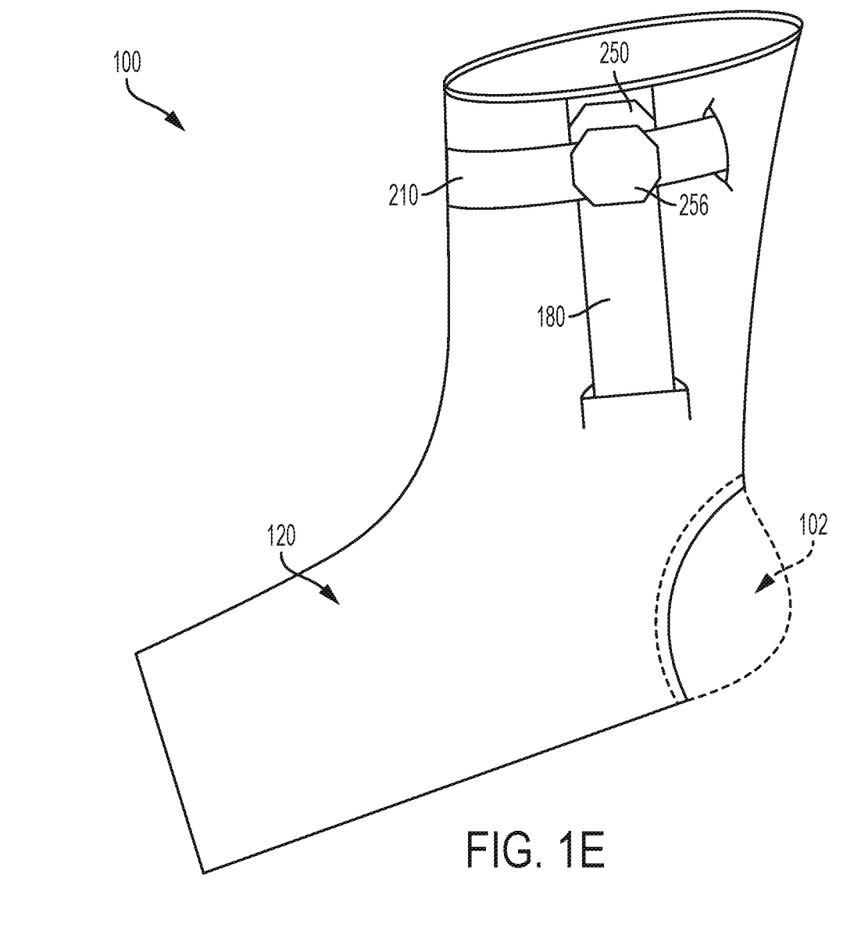
FIG. 1E is a medial side view of an ankle brace, according to an example embodiment of the present disclosure.

As illustrated in FIGS. 1C, 1D, and 1E, the collar strap 210 may only have a single exposed end (e.g., first end 212). The first end 212 of the collar strap 210 may include a tab 256, such as a thumb-tab. In an example, the collar strap 210 may include an attachment region 288. The attachment region 288 may include a hook and loop fastener such as VELCRO®, magnets, attachment holes, or the like along the length of the strap. For example, the collar strap 210 may include a hook and loop fastener such as VELCRO® on the outside surface, which enables the collar strap 210 to be positioned and secured around the user's leg. The attachment region 288 may extend along the entire length of the collar strap 210, or may extend along a portion of the collar strap 210. Additionally, the collar strap 210 may include a hook and loop fastener such as VELCRO®, magnets, or pins on the inside surface to engage the attachment region 288 on the outside surface of the collar strap 210. In another example, tab 256 may engage the attachment region 288 of the collar strap 210.

The ankle brace 100 may also include first and second attachment pads 290, 292. The attachment pads 290, 292 may be positioned on the outer sleeve 120 and may include a hook and loop fastener such as VELCRO®, magnets, attachment holes, or the like. The attachment pads 290, 292 may be aligned with the medial strap 180 and the lateral strap 200 and positioned near the top of the ankle brace 100 such that the medial and lateral straps 180, 200 may be tightened and secured to the attachment pads 290, 292.

In an example, the medial strap 180 and the lateral strap 200 may be tightened before the collar strap 210 is tightened. For example, the medial strap 180 may be positioned under the collar strap 210, tightened, and fixed to the first attachment pad 290. Likewise, the lateral strap 200 may be positioned under the collar strap 210, tightened, and fixed to the second attachment pad 292. Then, the collar strap 210 may be tightened thereby advantageously further securing the medial and lateral straps 180, 200 before being secured to the attachment region 288. For example, as illustrated in FIG. 1E, the medial strap 180 is positioned under the collar strap 210 and the collar strap 210 is tightened and fixed to the attachment region 288. In other examples, the medial strap 180 and/or the lateral strap 200 may be positioned over the collar strap 210.

Figure 1F:
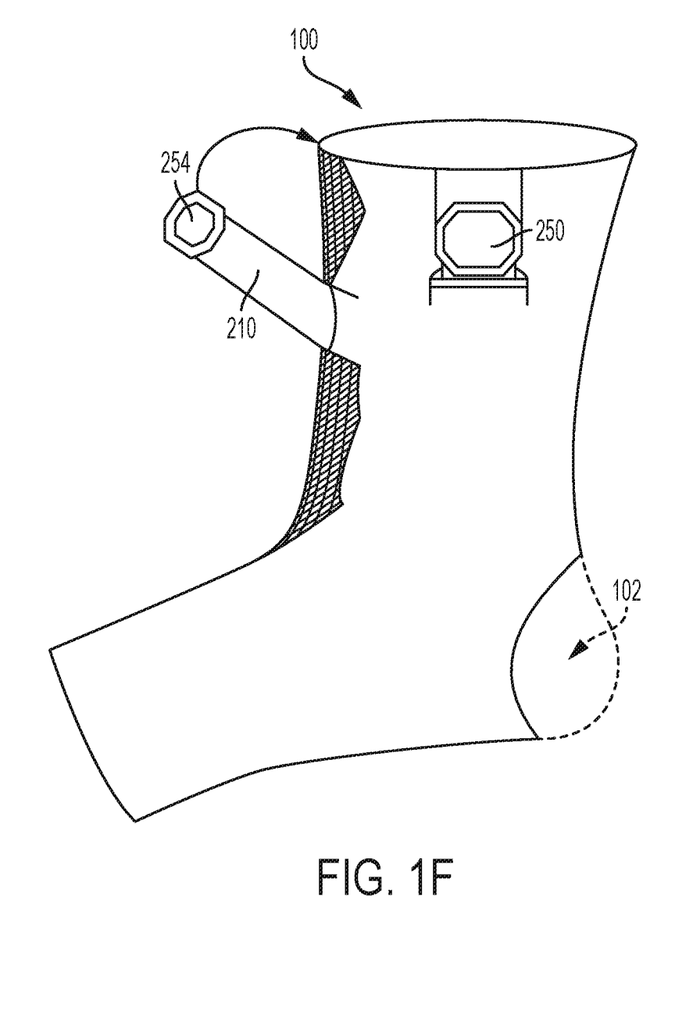
FIG. 1F is a medial side view of an ankle brace, according to an example embodiment of the present disclosure.

As illustrated in FIG. 1F, in an example embodiment, the collar strap 210 may be positioned under the outer sleeve 120, such that it is mostly concealed from the user. Additionally, the collar strap 210 my be positioned lower on the user's leg towards the user's sole such that it catches the medial and lateral straps 210 in an location closer to the user's foot. For example, the collar strap 210 may start at the front of the ankle brace 100 extending around the lateral side to the back of the user's foot, around the medial side of the ankle brace 100, and out through a slot near the front of the foot. The second end 214 may include a tab 254 that can be tightened and fixed to the ankle brace 100. For example, the medial strap 180 and the lateral strap 200 may be pre-positioned under the collar strap 210 such that tightening the collar strap further secures the medial and lateral straps 180, 200. As discussed above, once the lateral and medial straps 180, 200 are fastened, the collar strap 210 may be pulled tightly on the outwardly exposed tab 254 and then secured to the ankle brace 100. In an example, the collar strap 210 may cover the entire circumference of the ankle brace 100 such that it is positioned over the lateral and medial straps 180, 200.

Figure 1G:
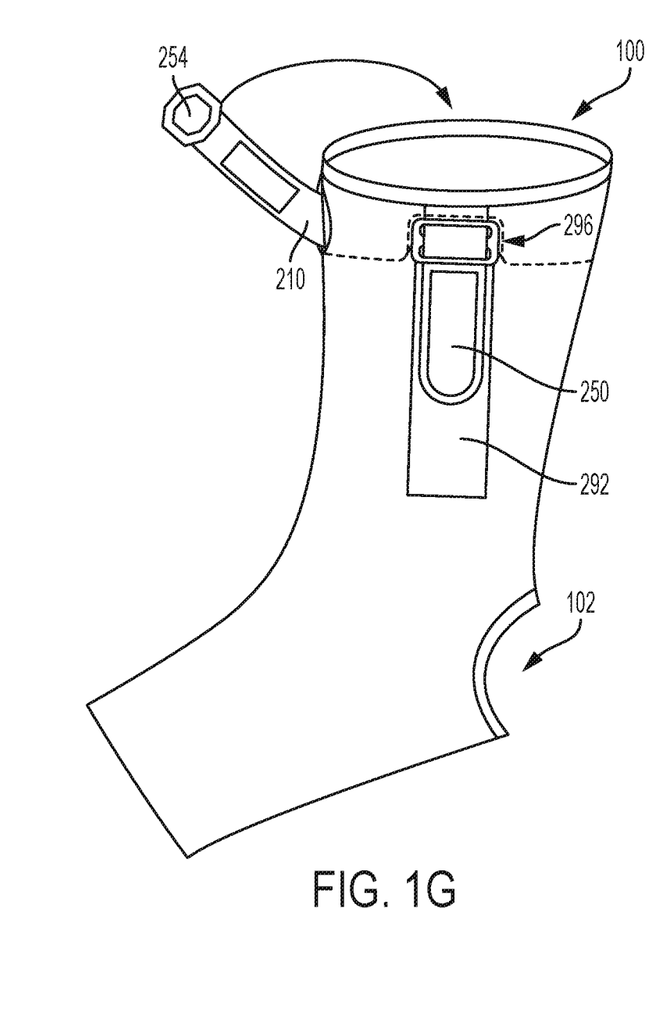
FIG. 1G is a medial side view of an ankle brace, according to an example embodiment of the present disclosure.

As illustrated in FIG. 1G, in an example embodiment, the ankle brace 100 may include one or more anchors or fasteners 296, such as a triglide, such that the medial strap 180 and/or the lateral strap 200 is tightened and then fastened in a downward orientation. For example, the medial strap 180 may include a hook and loop fastener such as VELCRO® or the like on the inside and outside surfaces of the strap such that the strap may be fastened to itself. Similarly, the lateral strap 200 may include a hook and loop fastener such as VELCRO® or the like on the inside and outside surfaces of the strap such that the strap may be fastened to itself. In other example embodiments, other fasteners may be used. Additionally, the ankle brace 100 may include attachment pads (e.g., attachment pads 290, 292) that the medial and lateral straps 180, 200 may attach to. Additionally, the tabs at the end of the medial and lateral straps 180, 200 (e.g., tab 250) may include flanges to prevent the straps from being fully pulled through the anchors or fasteners 296 and back into the ankle brace 100.

As illustrated in FIGS. 1A. 1B, 2A, and 2B, the inner sleeve 110 and the outer sleeve 120 may include one or more pockets. In an example embodiment, the outer sleeve 120 may include an arch support pocket 300. The arch support pocket 300 may be adapted to receive an arch support. In another example embodiment, the inner sleeve 120 may include the arch support pocket 300. Additionally the ankle brace 100 may include lateral support pockets designed to receive inserts on the medial and lateral sides of the foot. In another example embodiment, the ankle brace 100 may include a top pocket to insert protection shield on the top area of the foot. The pockets may be selectively closed by the user. For example, a pocket may be closed when not in use or closed after the associated support and/or shield has been positioned within the pocket. In an example embodiment, the pockets may be able to be closed using a hook and loop fastener such as VELCRO®, a zipper, a magnet, a snap, or the like.

Figure 2A:
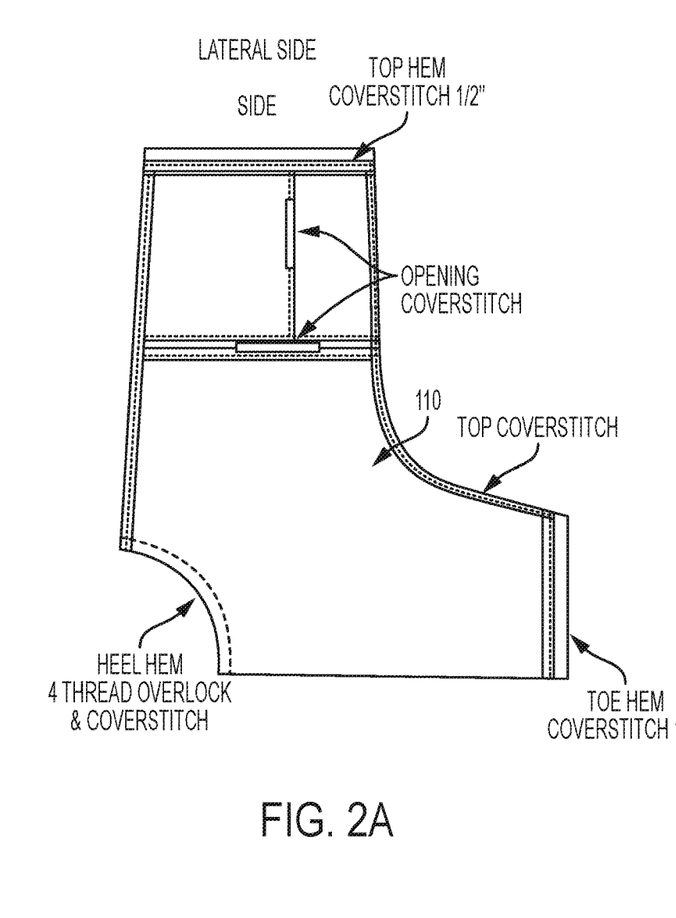
FIG. 2A is a lateral side view of an inner sleeve of an ankle brace, according to an example embodiment of the present disclosure.
Figure 2B:
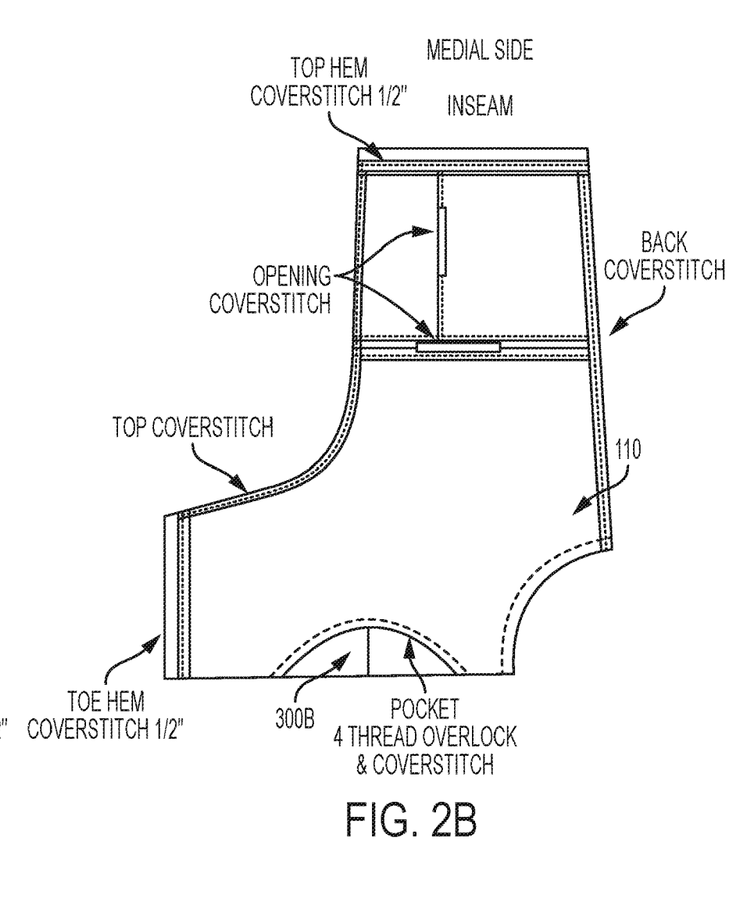
FIG. 2B is a medial side view of an inner sleeve of an ankle brace, according to an example embodiment of the present disclosure.

In an example embodiment, the outer sleeve 120 and the arch pocket 300 may be manufactured from a single material or multiple different materials. For example, the outer sleeve may be made of nylon, polyester, polyamide and Spandex® blends, seamless 2-way stretch fabric, 4-way stretch fabric, polyester and cotton blends, or be selected from primary and accent colors attributable to a sports team. The outer sleeve material may be adapted for anatomical contouring and may prevent the retention of body heat. As illustrated in FIG. 1B and FIG. 2B, the arch support pocket 300 may be sewn into the inner sleeve 110 or the outer sleeve 120. For example, the arch support pocket 300 may be positioned on the outside of the inner sleeve 110 to allow for easy insertion and egress of an orthotic arch support. In another example, the arch support pocket 300 may be positioned on the inside of a sleeve (e.g., inner sleeve 110 or outer sleeve 120) that can be turned inside and right side out to allow access to the arch support pocket 300. The arch support pocket 300 may be the same material as the inner sleeve 110 or the outer sleeve 120. In another example embodiment, the arch support pocket 300 may be a different material than the inner sleeve 110 and/or the outer sleeve 120 to provide additional comfort, support, and/or durability.

Figure 3A:
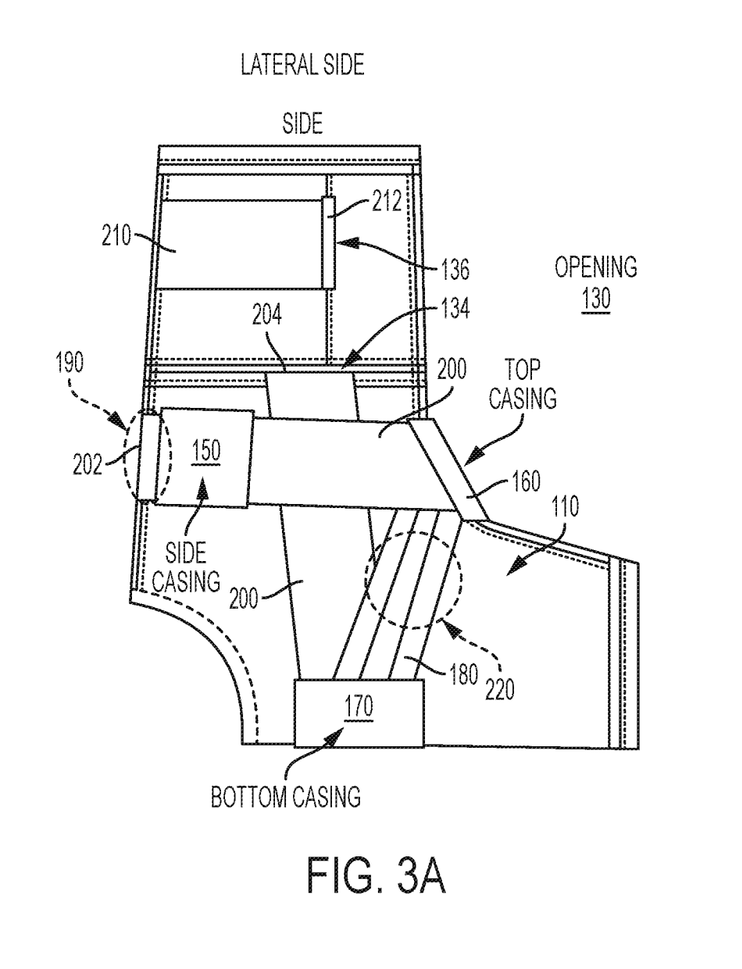
FIG. 3A is a lateral side view an inner sleeve and strap system of an ankle brace, according to an example embodiment of the present disclosure.
Figure 3B:
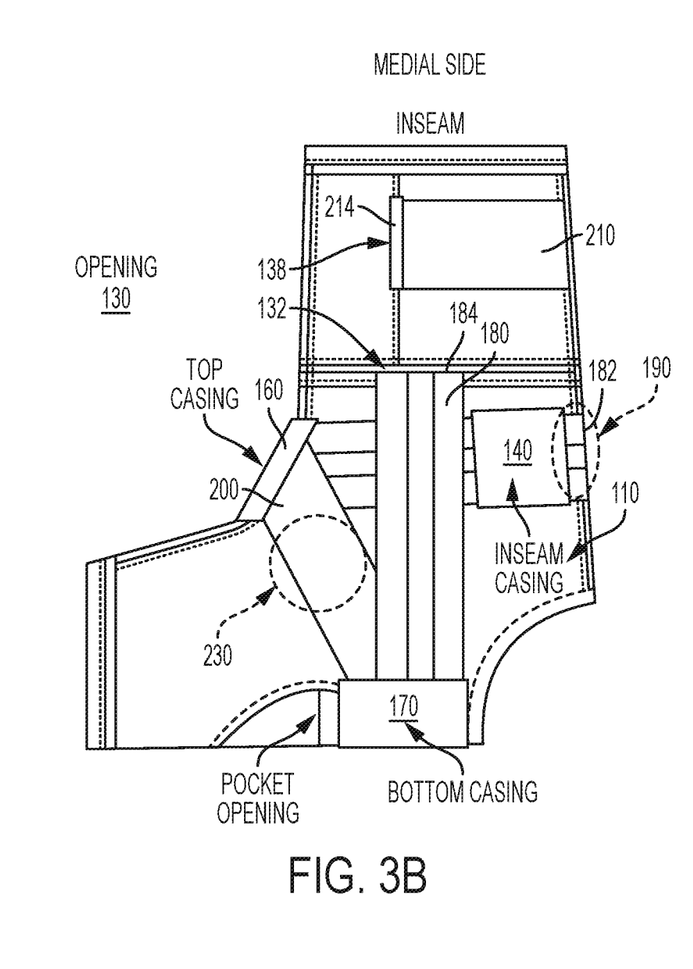
FIG. 3B is a medial side view of an inner sleeve and strap system of an ankle brace, according to an example embodiment of the present disclosure.

FIG. 3 is a view of an inner sleeve and strap system of an ankle brace, according to an example embodiment of the present disclosure. In an example embodiment, the structure and support the ankle brace provides to the user may be augmented with straps configured to tighten over the user's foot. For example, the straps may provide support directly, or augment support provided by other features embodied in the ankle brace 100. In other example embodiments, two or more straps may be used in combination to provide support directly, or augment support provided by other features embodied in the ankle brace 100. In other example embodiments, guides may be integrated within the ankle brace to route the straps to the correct location on the foot to provide maximum support or other function to the user.

As shown in the example embodiment in FIG. 3, the ankle brace 100 may include one or more guides coupled to the inner sleeve 110. In an example embodiment, the ankle brace 100 may include a medial guide 140 and a lateral guide 150. In another example embodiment, the ankle brace 100 may include a top guide 160 and a bottom guide 170. Additionally, the ankle brace 100 may include the medial guide 140, the lateral guide 150, the top guide 160, and the bottom guide 170. The medial guide 140, lateral guide 150, top guide 160 and/or the bottom guide 170 may be coupled to the inner sleeve 110. For example, the guides (e.g., medial guide 140, lateral guide 150, top guide 160 and/or the bottom guide 170) may be sewn or glued to the inner sleeve 110. The inner sleeve 110 may include any combination of the guides described above. Additionally, the inner sleeve 110 may include additional guides. In an example embodiment, each guide (e.g., lateral guide 150 or medial guide 140) may be a set of guides positioned in close proximity to each other. For example, the medial guide 140 may include two or more guides positioned next to each other that collectively function as the medial guide 140. In other embodiments, guides may be made of different materials.

The guides (e.g., medial guide 140, lateral guide 150, top guide 160 and/or the bottom guide 170) may form channels or pathways adapted to receive one or more straps. For example, a first channel may include a first end of the first channel, the medial guide 140, the top guide, the bottom guide, and a second end of the first channel. The first channel may be adapted to receive the medial strap. For example, a medial strap (discussed in more detail below) may pass through the first channel, which may extend from the achilles area, to the medial guide 140, to the top guide 160, over a lateral cuneiform area, to the bottom guide 170, and out from the first slot to the second end of the first channel. A second channel may include a first end of the second channel, the lateral guide 150, the top guide, the bottom guide 170, and a second end of the second channel. The second channel may be adapted to receive a lateral strap (discussed in more detail below). For example, the lateral strap may pass through the second channel, which may extend from the achilles area, to the lateral guide 150, to the top guide 160, over a medial cuneiform area, to the bottom guide 170, and out from the second slot to the second end of the second channel. A third channel may be adapted to receive a collar strap (discussed in more detail below).

The guides may be made of the same material as the inner sleeve 110 or from a different material than the inner sleeve 110. For example, the guides (e.g., medial guide 140, lateral guide 150, top guide 160 and/or the bottom guide 170) may be made from a rigid material. In another example embodiment, the guides may be made from a non-rigid material or a semi-rigid material. For example, the medial guide 140, lateral guide 150, top guide 160 and the bottom guide 170 may all be made from a rigid material. Conversely, the medial guide 140, lateral guide 150, top guide 160 and the bottom guide 170 may all be made from a non-rigid or semi-rigid material. In an example embodiment, the medial guide 140 and the lateral guide 150 may be made from a non-rigid material while the top guide 160 and the bottom guide 170 may be made from a rigid material. The guides (e.g., medial guide 140, lateral guide 150, top guide 160 and/or the bottom guide 170) may include any configuration of guides and materials as described above.

In an example embodiment, the bottom guide 170 may be made of a thin non-rigid material, which advantageously provides guiding functionality and reduces bulk near the bottom of the ankle brace 100, which may affect fit and cause the user discomfort. The guides may be sufficiently durable to withstand repeated tight strapping while also being resistant to tearing with repeated heavy use. For example, the guides may be made of a very strong material such as but not limited to leather, metal cord, braided nylon, or the like.

The guides may have a predetermined geometry to provide sufficient guiding. Additionally, the guides may have a predetermined geometry to minimizing the bulkiness of the ankle brace. In an example embodiment, the guides (e.g., medial guide 140, lateral guide 150, top guide 160 and/or the bottom guide 170) may be configured to provide a long guide channel. For example, the guides may have various geometries and dimensional ranges based on the user's foot size. For example, the lateral guide 150 and medial guide 140 may extend from the achilles area 190 to the top guide 160. Additionally, the top guide 160 may extend to the bottom guide 170 such that the top guide 160 and bottom guide 170 connect. In another example embodiment, the top guide 160, bottom guide 170, medial guide 140, and lateral guide 150 may all be connected such that all four guides function as a single guide. Combining all guides into a single guide has the advantage of restricting the strap or straps, such as a medial strap 180 or a lateral strap 200 (described in more detail below), such that the straps may only move within the areas restricted by the combined guides, which may be more accurately described as channels in such an example embodiment.

The ankle brace 100 may include a medial strap 180. The medial strap 180 may be made of several different materials including but not limited to nylon (e.g. woven nylon), elastic, elastic blends, rubber, and the like. The medial strap 180 includes a first end 182 and a second end 184. In an example embodiment, the medial strap 180 may be positioned around the user's ankle 70 between the inner sleeve 110 and the outer sleeve 120. The medial strap 180 may be configured to tighten the inner sleeve 110. For example, the first end 182 of the medial strap 180 may begin at an achilles area 190, and the second end 184 of the medial strap 180 may protrude from a first slot 132 of the plurality of slots 130 in the outer sleeve 120 such that when the user pulls on a medial tab 184, the medial strap creates a tension force between the achilles area 190, a plurality of guides, and the medial tab 184 thereby tightening the inner sleeve around the users foot as well as pressure or support on the user's achilles area 190, arch, ankle, and/or lateral cuneiform 220. Such an example embodiment may include a first channel that includes the top guide 160, bottom guide 170, and the medial guide 140 that the medial strap 180 creates tension across.

The ankle brace 100 may also include a lateral strap 200. The lateral strap 200 may be made of several different materials including but not limited to nylon (e.g., woven nylon), elastic, elastic blends, rubber, and the like. In an example embodiment, the medial strap may be made of a second material, such as nylon. The lateral strap 200 includes a first end 202 and a second end 204. In an example embodiment, the lateral strap 200 may be positioned around the user's ankle 70 between the inner sleeve 110 and the outer sleeve 120. The lateral strap 200 may be configured to tighten the inner sleeve 110. For example, the first end 202 of the lateral strap 200 may begin at an achilles area 190, and the second end 204 of the lateral strap 200 may protrude from a second slot 134 of the plurality of slots 130 in the outer sleeve 120 such that when the user pulls on a lateral tab 204, the lateral strap creates a tension force between the achilles area 190, a plurality of guides, and the lateral tab 204 thereby tightening the inner sleeve around the users foot as well as pressure or support on the user's achilles area 190, arch, ankle, and/or medial cuneiform 230. Such an example embodiment may include a top guide 160, bottom guide 170, and a lateral guide 150 that the lateral strap 200 creates tension across.

The ankle brace 100 may also include a collar strap 210. The collar strap 210 includes a first end 212 and a second end 214. The collar strap 210 may be configured to prevent the ankle brace 100 from slipping down the leg of the user. The collar strap 210 in general may be placed along the top portion of an ankle brace 100 to prevent the ankle brace from slipping down the leg of the user. In an example embodiment, the collar strap 210 may be placed along the top of the ankle brace such that the collar strap 210 sits at the height of a crew sock. In another example embodiment, an ankle brace 100 may extend substantially up the user's leg. In such an embodiment, the collar strap 210 may be positioned farther up the user's leg, closer to the user's calf or even the user's knee. In another example embodiment, several collar straps may be used throughout the length of the ankle brace that extends up the user's leg. For example, the ankle brace 100 may include a lower collar strap close to the user's ankle, another collar strap at the height of a crew sock, and an upper collar strap around the user's calf. The collar strap 210 may be made of several different materials including but not limited to nylon (e.g., woven nylon), elastic, elastic blends, rubber, or the like.

The collar strap 210 may be adapted to enforce a rigid support in the ankle brace 100. In an example embodiment, the ankle brace 100 may be configured to allow rigid supports to be inserted between the inner sleeve 110 and the outer sleeve 120. Such a rigid support may be made from very rigid materials such as metal, hard plastic, polymer, metals, alloys, rubber, cushioning gel, or a combination thereof. In other embodiments, a rigid support may be made from an inflatable membrane than can be filled with gel, liquids, gases (e.g., air or water), thus allowing the rigidity of the membrane to be variable based on the user's desire. In either variation of a rigid insert, the collar strap 210 may be designed to hold the insert in place, which advantageously restricts sliding, rubbing, or other movement of the rigid or semi-rigid support, which can prevent blistering or chafing of the user's leg. For example, the above embodiment may be especially advantageous with an ankle brace designed to be worn while participating in sports.

The collar strap 210 may be positioned around a tibia 80 and a fibula 90 of the user between the inner sleeve 110 and the outer sleeve 120 of the ankle brace 100. The first end 212 of the collar strap 210 may protrude from a third slot 136 of the plurality of slots 130 and the second end 214 of the collar strap 210 may protrude from a fourth slot 138 of the plurality of slots 130 in the outer sleeve 120. The collar strap 210 may be configured to move freely between the third slot 136 and the fourth slot 138 of the plurality of slots 130. In an example embodiment, the collar strap 210 may be configured to tighten the inner sleeve 110 around the user's tibia and fibula such that the ankle brace 100 maintains a predetermined height on the user's ankle, which advantageously prevents the ankle brace 100 from sliding down the user's leg and foot during use. In such an embodiment, a collar strap may be manufactured from the same or different material from the medial strap 180 or the lateral strap 200.

In an example embodiment, the medial strap 180 may be made of a first material and the lateral strap 200 may be made of a second material. The first material and the second material may be the same material, such as nylon, or the first material and the second material may be different materials. Additionally, the collar strap 210 may be made of the same material as the medial strap 180 and/or the lateral strap 200. In another embodiment, the collar strap 210 may be made of a different material than the medial strap 180 and/or the lateral strap 200. In addition, the collar strap may be manufactured to a different specification than the medial strap 180 and/or the lateral strap 200. In an example embodiment, the collar strap 210 may be configured to sit outside of the shoe. Additionally, the medial strap 180 and the lateral strap 200 may be configured to sit within the ankle brace (e.g., inside of a shoe while the user is wearing a shoe). For example, the collar strap 210, which is less restricted, may be thicker and wider than the medial and lateral straps 180, 200. For example, the additional width and thickness of the collar strap 210 may advantageously increase the strength of the collar strap 210.

In another example embodiment, the medial strap 180, lateral strap 200 and/or collar strap 210 may have different widths. In an example, each strap may be approximately 1 to 2 inches wide. In other examples, the straps may be wider (e.g., have a width greater than 2 inches) or may have a width of less than 1 inch. In another example embodiment, the medial strap may have a predetermined width to ensure fitment underneath a user's shoe. For example, the medial strap 180 may be 1 to 2 inches wide. The lateral strap may not have such a restriction, and the lateral strap may be thicker and/or wider to allow the ankle brace to be stronger and able to withstand more aggressive tightening by the user. Additionally, the collar strap 210 may be thicker and/or wider than the other straps (e.g., medial strap 180 and lateral strap 200 to allow a user to get a very tight fit for the upper portion of the ankle brace 100, and to reduce sliding or slipping of the ankle brace on the user's leg. Similarly, the lateral strap 200 and/or the collar strap 210 may have the smallest width.

The ankle brace 100 may also include a plurality of adjustable openings or slots 130. In an example embodiment, the ankle brace 100 may include at least one adjustable opening with a tab extending from the adjustable opening. The tab may be connected to a strap which may tighten around the user's foot (described in more detail below), providing support when the tab is pulled. In another example embodiment, the ankle brace 100 may include four separate adjustable openings. The plurality of slots 130 may be designed such that a tab extends from each of the plurality of adjustable openings 130. For example, on the medial side, a first tab 250 may extend from the outer sleeve 120, discussed in more detail below, through a first slot 132. The first slot 132 may be positioned on the medial side of the foot and oriented in a horizontal direction (e.g., orients strap in horizontal direction). The first tab 250 may be connected to the second end 184 of the medial strap 180. Additionally, a third tab 254 may extend from the outer sleeve 120 through a fourth slot 138. The fourth slot 138 may be positioned on the medial side of the tibia and oriented in a vertical direction (e.g., orients strap in vertical direction). The third tab 254 may be coupled to the second end 214 of the collar strap 210. On the lateral side, a second tab 252 may extend from the outer sleeve 120 through a second slot 134. The second slot 134 may be positioned on the lateral side of the foot and oriented in the horizontal direction (e.g., orients strap in horizontal direction). The second tab 252 may be coupled to the second end 204 of the lateral strap 200. Additionally, a fourth tab 256 may extend from the outer sleeve 120 through a third slot 136. The third slot 136 may be positioned on the lateral side of the fibula and oriented in the vertical direction (e.g., orients strap in vertical direction). The fourth tab 256 may be coupled to the first end 212 of the collar strap 210.

In other example embodiments, the medial strap and the lateral strap may be routed dependent on the desired result from wearing the brace, the comfort of the user when wearing the brace, or the design of a shoe into which the ankle brace may be integrated. In an example embodiment the medial strap 180 may extend from the first end 182 positioned at the achilles area 190, through the medial guide 150, through the top guide 160, over a lateral cuneiform 220, through the bottom guide 170, and out from the first slot 132 to the second end 184 of the medial strap 180. The lateral strap 200 may extend from the first end 202 positioned at the achilles area 190, through the lateral guide 140, through the top guide 160, over a medial cuneiform 230, through the bottom guide 170, and out from the second slot 134. In an example embodiment, the medial guide may be configured to guide the medial strap in a substantially horizontal direction to the top guide. The lateral guide may be configured to guide the lateral strap in a substantially horizontal direction to the top guide. Additionally, the top guide may be configured to guide the medial strap in a first diagonal direction to the bottom guide. Similarly, the top guide may be configured to guide the lateral strap in a second diagonal direction to the bottom guide. The bottom guide may be configured to guide the medial strap around the bottom of the foot to a substantially vertical orientation adjacent the medial guide. Similarly, the bottom guide may be configured to guide the lateral strap around the bottom of the foot to a substantially vertical orientation adjacent the lateral guide.

In other example embodiments, the medial strap and/or lateral strap may be wound around the ankle in a FIG. 8 pattern. For example, a strap may start at the achilles area 190, extend through the lateral guide 140, through the top guide 160, cross over the medial cuneiform 230, cross through the bottom guide 170, extend over the lateral cuneiform 220, back through the top guide 160, and end back again at the achilles area 190. A FIG. 8 embodiment may be repeated with multiple straps, or overlaid several times with the same strap, which can result in a more rigid or more compressed ankle brace. Such an embodiment may also clasp at the achilles area through a means of attaching the ends of the strap, or by attaching a single end to the outer sleeve of the ankle brace. In an example embodiment where a strap clasps at the achilles area, an ankle brace outer sleeve may include additional slots to allow a strap to extend from the outer sleeve 120 to allow the user to tighten the strap an affix the strap such that the desired tightness of the strap is maintained. Such means for attachment for a strap in the achilles area may include but are not limited to snaps, buttons, shoelaces, tying the strap ends, a hook and loop fastener such as VELCRO®, triglides, magnets, or a gear system that enables a user to tighten the strap by activating a knob, lever, or the like of the gear system.

Figure 4A:
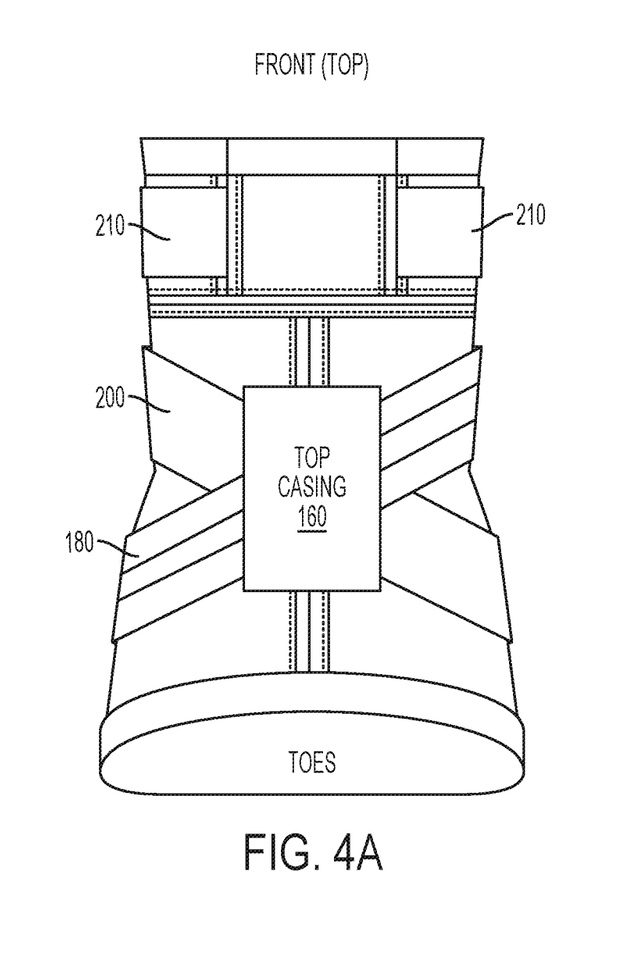
FIG. 4A is a top view of an inner sleeve and bottom view of an inner sleeve of an ankle brace, according to an example embodiment of the present disclosure.
Figure 4B:
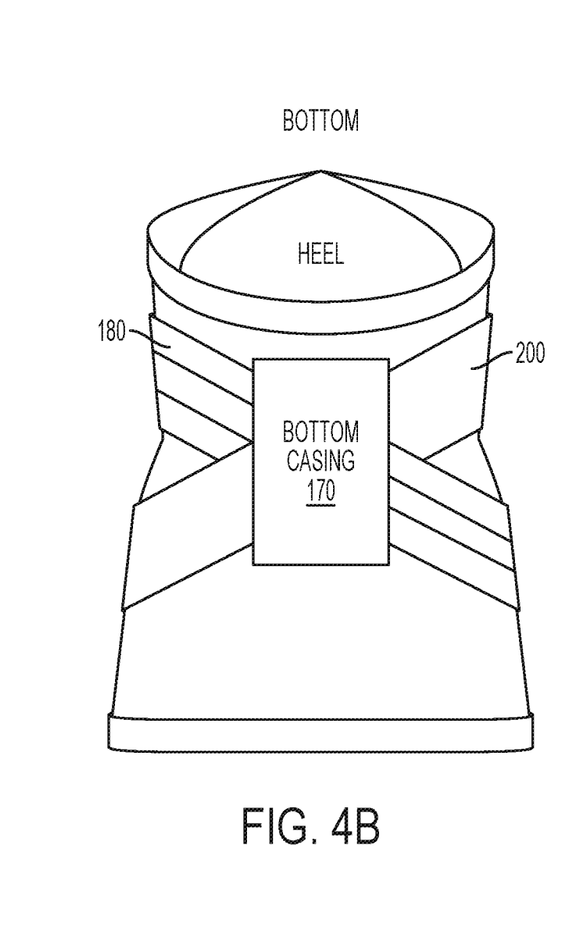
FIG. 4B is a bottom view of an inner sleeve of an ankle brace, according to an example embodiment of the present disclosure.

FIG. 4A and FIG. 4B are top and bottom views of an inner sleeve of an ankle brace, according to an example embodiment of the present disclosure. As illustrated in FIG. 4A, the medial strap 180 and the lateral strap 200 may cross over the front of a foot 50 and through the top guide 160. Furthermore, the collar strap 210 may wraps around a leg toward the front of the foot 50. As illustrated in FIG. 4B, the medial strap 180 and the lateral strap 200 may cross underneath the user's foot 50 and through the bottom guide 170. In other example embodiments, the ankle brace 100 may not include a bottom guide 170 and instead rely on the shape of the user's foot to hold a strap routed underneath the user's foot. In another example embodiment, the bottom guide 170 may be designed to be integrated with other features included on the bottom of an ankle brace 100 such as an insole, an arch support insert, or a shoe or boot. In an example embodiment, the ankle brace 100 may be affixed to an athletic shoe, a ski boot, a snowboard boot, or the like.

Figure 5:
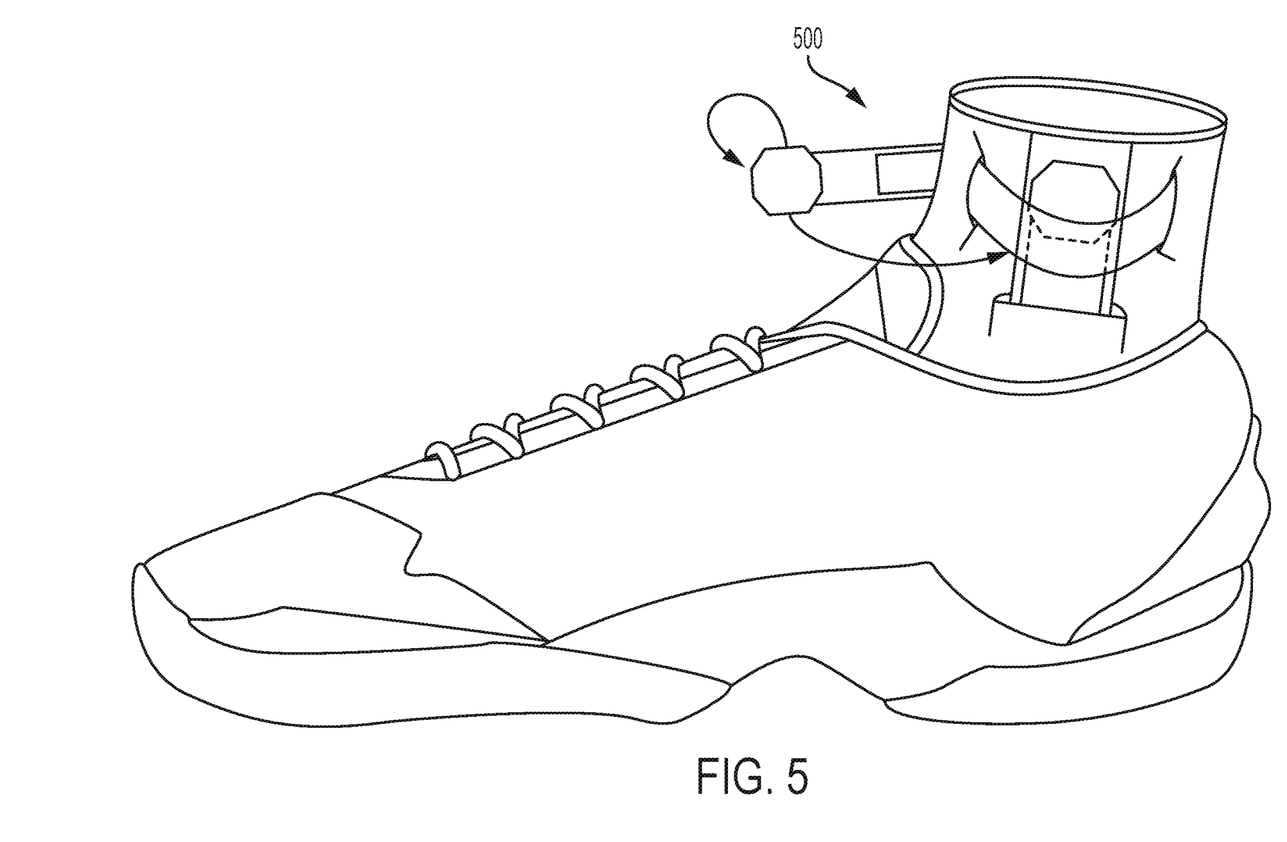
FIG. 5 is a side view of an ankle brace integrated into an athletic shoe, according to an example embodiment of the present disclosure.

As illustrated in FIG. 5, in an example embodiment, the ankle brace 500 may integrated into a shoe, such as an athletic shoe. The ankle brace 500 may include each of the features described above.

In another example embodiment, ankle brace 100, 500 may include a sensor module. For example, the sensor module may include a microchip processor and one or more sensors to sense various conditions including speed, acceleration, positioning, impact, etc. that may later be used for athletic applications. For example, the sensor module may collect data that can be used for sports training, physical therapy, etc. The above description is exemplary of the features of the system disclosed herein. It should be understood that various changes and modifications to the presently disclosed embodiments may be apparent to those skilled in the art. Such changes and modifications may be made without departing from the spirit and scope of the present subject matter and without diminishing its intended advantages. It is therefore intended that such changes and modifications be covered by the appended claims.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims. Also, it should be appreciated that the features of the dependent claims may be embodied in the systems, methods, and apparatus of each of the independent claims.

The invention claimed is:

1. An ankle brace comprising:
   an inner sleeve adapted to fit over a foot, a heel, and an ankle of a user;
   an outer sleeve adapted to fit over the inner sleeve, the outer sleeve including a plurality of slots positioned in and around the outer sleeve;
   a medial guide coupled to the inner sleeve;
   a lateral guide coupled to the inner sleeve;
   a top guide coupled to the inner sleeve;
   a bottom guide coupled to the inner sleeve;
   a medial strap of a first material having a first end and a second end adapted to be positioned around the user's ankle between the inner sleeve and the outer sleeve, wherein
   the medial strap is configured to tighten the inner sleeve,
   the first end of the medial strap is configured to begin at an Achilles area, wherein the Achilles area is an area of the foot where an Achilles tendon is located, and the second end of the medial strap protrudes from a first slot of the plurality of slots in the outer sleeve;

a lateral strap of a second material having a first end and a second end adapted to be positioned around the user's ankle between the inner sleeve and the outer sleeve, wherein the lateral strap is configured to tighten the inner sleeve, the first end of the lateral strap is configured to begin at the Achilles area, and the second end of the lateral strap protrudes from a second slot of the plurality of slots in the outer sleeve;

and a collar strap of a third material having a first end and a second end adapted to be positioned around a tibia and a fibula of the user between the inner sleeve and the outer sleeve, the first end of the collar strap protrudes from a third slot of the plurality of slots in the outer sleeve, wherein the collar strap is configured to tighten the inner sleeve such that the ankle brace is configured to maintain a predetermined height on the user's ankle, the medial strap is configured to extend from the first end positioned at the Achilles area, through the medial guide, through the top guide, over a lateral cuneiform, through the bottom guide, and out from the first slot to the second end of the medial strap respectively, the lateral strap is configured to extend from the first end positioned at the Achilles area, through the lateral guide, through the top guide, over a medial cuneiform, through the bottom guide, and out from the second slot respectively, wherein the top guide is positioned on a top side of the ankle brace and the bottom guide is positioned on a bottom side of the ankle brace, wherein the bottom side of the ankle brace is configured to correspond to a bottom side of the foot, and the collar strap is configured to move freely between the third slot and a fourth slot of the plurality of slots.

2. The ankle brace of claim 1 further including a pocket between the inner sleeve and the outer sleeve and adapted to be positioned underneath the user's foot, wherein the pocket is adapted to receive an arch support insert.

3. The arch support insert of claim 2, wherein the arch support insert is adjustable by the user.

4. The ankle brace of claim 1, wherein the first slot is adapted to be positioned on a medial side of the foot and oriented in a horizontal direction.

5. The ankle brace of claim 1, wherein the second slot is adapted to be positioned on a lateral side of the foot and oriented in a horizontal direction.

6. The ankle brace of claim 1, wherein the third slot is adapted to be positioned on a lateral side of the fibula and oriented in a vertical direction.

7. The ankle brace of claim 1, wherein the fourth slot is adapted to be positioned on a medial side of the tibia and oriented in a vertical direction.

8. The ankle brace of claim 1, wherein the first material, the second material, and the third material are the same.

9. The ankle brace of claim 1, wherein the inner sleeve is made from a non-slip material.

10. The ankle brace of claim 1, wherein the outer sleeve is made from a breathable mesh material.

11. The ankle brace of claim 1, wherein the ankle brace is affixed to one of an athletic shoe, a ski boot, and a snowboard boot adapted to receive the ankle brace.

12. An ankle brace comprising:

an inner sleeve adapted to fit over a foot, a heel, and an ankle of a user;

an outer sleeve adapted to fit over the inner sleeve, the outer sleeve including a plurality of slots positioned around the outer sleeve;

a first channel adapted to receive a medial strap, wherein the first channel includes a first end, a medial guide, a top guide, a bottom guide, and a second end, wherein the top guide is positioned on a top side of the ankle brace and the bottom guide is positioned on a bottom side of the ankle brace, wherein the bottom side of the ankle brace is configured to correspond to a bottom side of the foot, the first end of the first channel is adapted to be positioned at an Achilles area, wherein the Achilles area is an area of the foot where an Achilles tendon is located, and the first channel is configured to extend from the Achilles area, to the medial guide, to the top guide, over a lateral cuneiform area, to the bottom guide, and out from a first slot of the plurality of slots to the second end of the first channel;

a second channel adapted to receive a lateral strap, wherein the second channel includes a first end, a lateral guide, the top guide, the bottom guide, and a second end, the first end of the second channel is adapted to be positioned at the Achilles area, the second channel is configured to extend from the Achilles area, to the lateral guide, to the top guide, over a medial cuneiform area, to the bottom guide, and out from a second slot of the plurality of slots to the second end of the second channel; and a third channel adapted to receive a collar strap, wherein the inner sleeve and outer sleeve are coupled together to form an attached area and channel area, the channel area includes the first channel, the second channel, and the third channel, the medial strap is configured to move freely within the first channel, the lateral strap is configured to move freely within the second channel, and the collar strap is configured to move freely within the third channel.

13. The ankle brace of claim 12, wherein the outer sleeve includes a first attachment pad, the medial strap includes a first end and a second end, and the second end of the medial strap includes a second attachment pad, the second attachment pad is configured to be removably attached to the first attachment pad.

14. The ankle brace of claim 13, wherein the outer sleeve includes a third attachment pad, the lateral strap includes a first end and a second end, and the second end of the lateral strap includes a fourth attachment pad, the fourth attachment pad is configured to be removably attached to the third attachment pad.

* * * * *